United States Patent [19]

Hurrell

[11] Patent Number: 4,752,216

[45] Date of Patent: Jun. 21, 1988

[54] PROGRAMMED TEMPERATURE CONTROL OF A THERMAL SYSTEM

[75] Inventor: Ronald A. Hurrell, Marlow, England

[73] Assignee: The Perkin-Elmer Corporation, Norwalk, Conn.

[21] Appl. No.: 930,982

[22] Filed: Nov. 13, 1986

Related U.S. Application Data

[63] Continuation of Ser. No. 791,014, Oct. 24, 1985, abandoned.

[30] Foreign Application Priority Data

Dec. 3, 1984 [GB] United Kingdom ................ 8430484

[51] Int. Cl.<sup>4</sup> ........................ F27D 19/00; F27B 9/28
[52] U.S. Cl. ...................................... 432/48; 432/59; 432/72; 432/152
[58] Field of Search ...................... 432/24, 48, 59, 72, 432/152; 236/DIG. 9; 98/32, 33.1, 33.6, 34.6, 38.5, 38.6, 38.7

[56] References Cited

U.S. PATENT DOCUMENTS

| | | | |
|---|---|---|---|
| 2,034,700 | 3/1936 | Lorenz | 98/32 |
| 2,737,879 | 3/1956 | Cooke et al. | 98/119 |
| 3,170,681 | 2/1965 | Davies | 432/72 |
| 3,409,043 | 11/1968 | Warren, Jr. | 98/38.7 |
| 3,787,171 | 1/1974 | Cromp | 432/59 |
| 3,874,091 | 4/1975 | Fukumoto | 432/59 |
| 3,984,198 | 10/1976 | Birke et al. | 432/59 |
| 4,103,599 | 8/1978 | Walker | 98/34.6 |
| 4,111,643 | 9/1978 | Welland | 432/48 |
| 4,162,141 | 7/1979 | West | 432/152 |
| 4,407,446 | 10/1983 | Iijima et al. | 236/DIG. 9 |
| 4,591,517 | 5/1986 | Whipple et al. | 432/59 |

FOREIGN PATENT DOCUMENTS

| | | |
|---|---|---|
| 0086421 | 8/1983 | European Pat. Off. . |
| 3329855 | 4/1984 | Fed. Rep. of Germany . |
| 2168334 | 8/1973 | France . |
| 211855 | 7/1984 | German Democratic Rep. . |

OTHER PUBLICATIONS

Abstracts of Japan, vol. 6, No. 232 (M-172) (1110), Nov. 18, 1982, M Field.

Primary Examiner—Henry C. Yuen
Attorney, Agent, or Firm—Ronald G. Cummings; Francis L. Masselle; Edwin T. Grimes

[57] ABSTRACT

The invention resides in the temperature control of the oven of a gas chromatograph. A variable speed fan circulates air within the oven. Vents in the oven wall open automatically in response to pressure imbalances between the ambient atmosphere and the oven interior. Temperature is controlled by regulated exchanges of ambient and oven air produced by variations in fan speed.

20 Claims, 3 Drawing Sheets

PROGRAMMED TEMPERATURE CONTROL OF A THERMAL SYSTEM

This is a continuation of co-pending application Ser. No. 791,014 filed on 10/24/85, abandoned.

TECHNICAL FIELD

The field of this invention is the control of temperature in a thermal system—more specifically, to the programmed temperature control of the oven of a gas chromatographic system.

BACKGROUND ART

It is conventional in gas chromatography to position the chromatographic column within an oven which is then programmed through a preselected temperature cycle to assist in the elution of components from a sample. The ovens of such systems commonly include fans which function to maintain even heat distribution and expedite cooling during portions of the temperature cycle.

In a conventional chromatographic oven, the fan speed remains essentially constant. However, the oven enclosure includes inlet and outlet vents which are adjusted mechanically, such as by means of solenoid actuators, stepping motors, or other separately energized mechanical devices. An example of one such arrangement is disclosed in U.S. Pat. No. 4,111,643 of Welland. If the need for such controls could be avoided, it will be apparent that a lower cost system would be feasible.

Another disadvantage of prior art controls is that the full range of air circulation volume is controlled by the size of the inlet and outlet air openings. This is because the fixed speed of the fan establishes an upper limit on the volumetric air flow rate. Therefore, increasing the area of the openings does not necessarily result in a proportional increase in air flow.

DISCLOSURE OF INVENTION

In accordance with the present invention, a gas chromatographic oven includes a variable speed fan with relatively well-defined low and high pressure regions induced by the fan. Automatically self-operating inlet and outlet vents are provided in the oven enclosure. These vents are operated by pressure differentials existing between the oven interior and the ambient atmosphere.

BEST MODE FOR CARRYING OUT THE INVENTION

Figure 1:
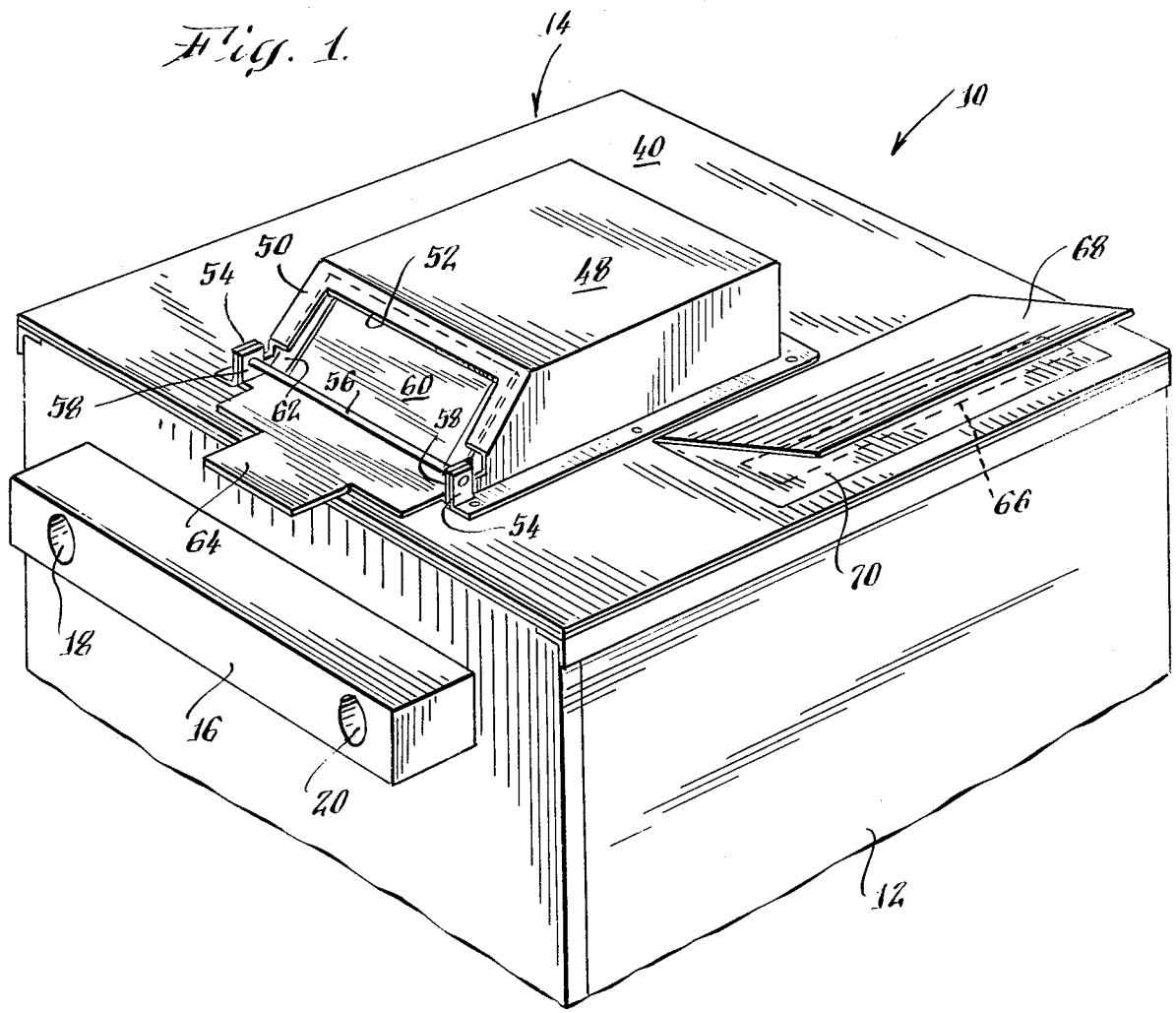
FIG. 1 is a perspective view of the oven portion of a gas chromatograph incorporating the invention.

With particular reference to FIGS. 1-5, there is illustrated a gas chromatograph oven 10 in the form of a rectangular housing 12 having insulated side walls and an open top. The top is closed by a flat, square, heat insulated, removable lid 14. Mounted externally along the front wall of oven 10 is a rectangular column support block 16. At one end of the column support block 16 is an injector opening 18 and at the other end is a detector opening 20. Internally of the oven, the ends of a chromatographic column 22 are connected to these openings via couplings 24 in a conventional manner. The injector and detector carried by the support block 16 form no part of this invention and, accordingly, are neither shown nor described. Mounted below the column 22 is an annular fan guard plate 26 which is positioned by means of radial tongues 28 extending into cooperating slots 30 in the oven side walls. Directly below the fan guard plate 26 is a fan impeller 32 of the central intake, radial discharge type. A shaft 34 from a variable speed motor 36 extends upwardly through a horizontal wall 38 and is connected to drive the impeller 32.

An important feature of this invention resides in the construction of the oven lid 14. As will be clear from FIG. 4, it is, in form, a sandwich of external 40 and internal 42 sheet metal layers enclosing an insulating material 44 and shaped along its edges to fit snugly but removably within the side walls of the oven housing 12. The lid 14 defines a central circular air inlet opening 46 which is enclosed by a housing 48 of generally rectangular cross-section but with a sloping front wall 50 defining a rectangular opening 52. Extending upwardly from the bottom of the housing 48, at either side of the opening 52, is a pivot support tab 54. A pivot rod 56 extends between the spaced pivot support tabs 54.

Figure 4:
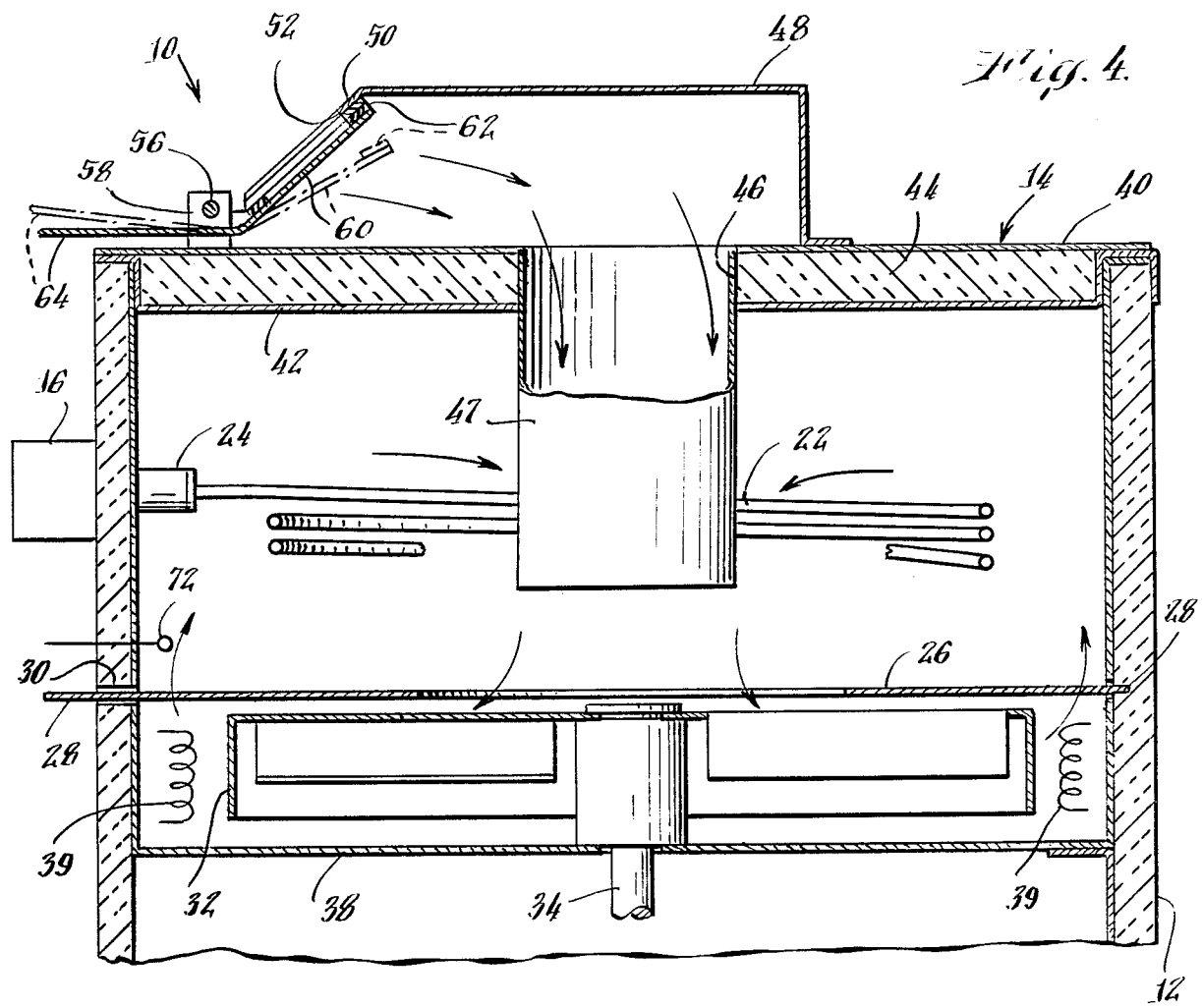
FIG. 4 is an enlarged cross-section taken substantially along the line 4—4 of FIG. 2.

Depending from the pivot rod 56 by a pair of spaced pivot tabs 58 is an air inlet door 60 which includes an upwardly angled portion carrying a peripheral rubber-like gasket 62 positioned to close the opening 52, as shown in FIG.4, and a generally horizontally extending counterweight portion 64. In the absence of moving forces, the door 60 assumes a closed position as illustrated by the solid lines of FIG. 4 but is pivotal to an open position, as indicated by the dash-dotted lines.

Figure 5:
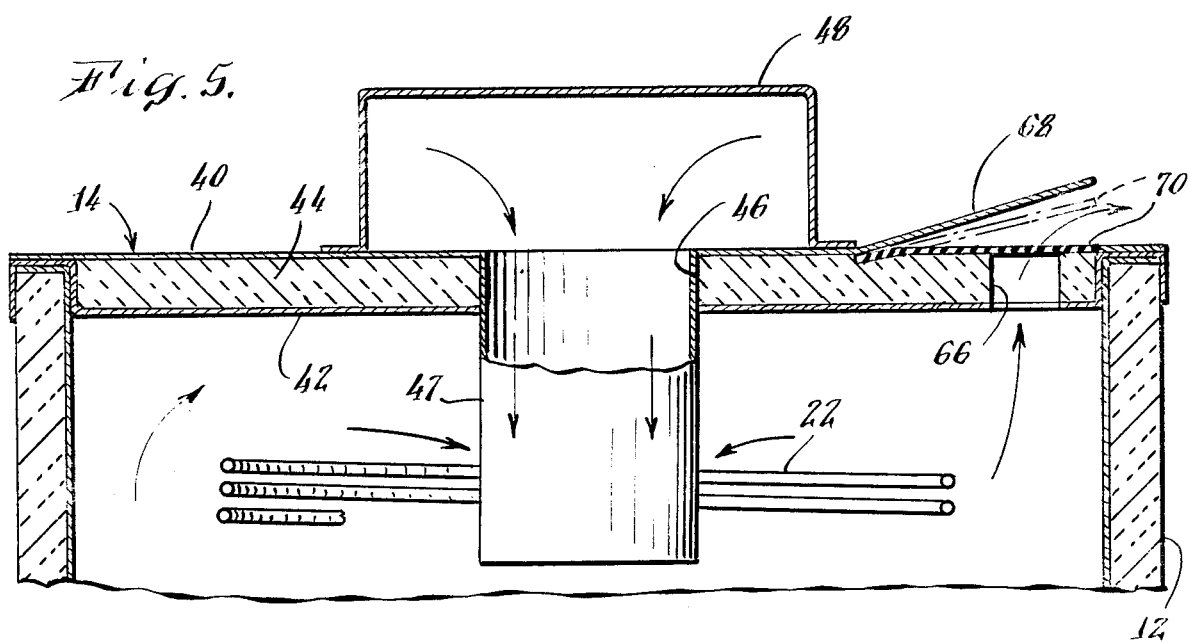
FIG. 5 is an enlarged partial cross-section taken substantially along the line 5—5 of FIG. 2.

Referring now to FIG. 5, it will be noted that the lid 14 also defines a rectangular air outlet opening 66 adjacent the external periphery of the oven. A rectangular portion of the outer sheet metal layer 40 is cut out and bent upward to form a deflector plate 68 overlying opening 66. Opening 66 is closed by a rectangular rubber-like flap 70 which normally lies flat against the top of the opening 66 but is movable upwardly under the influence of air flow to a position as illustrated by the dash-dotted lines of FIG. 5.

Figure 6:
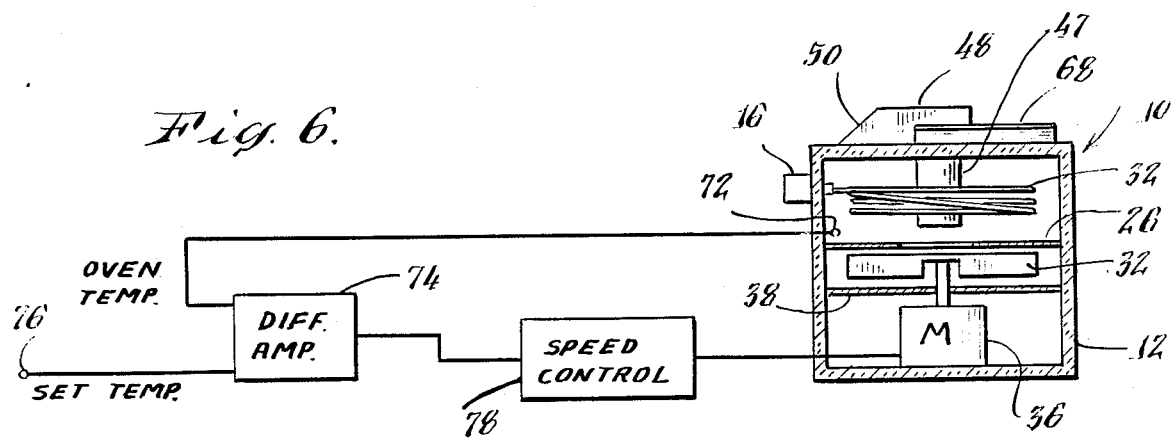
FIG. 6 is a schematic diagram of a control system usuable with the present invention.
Figure 2:
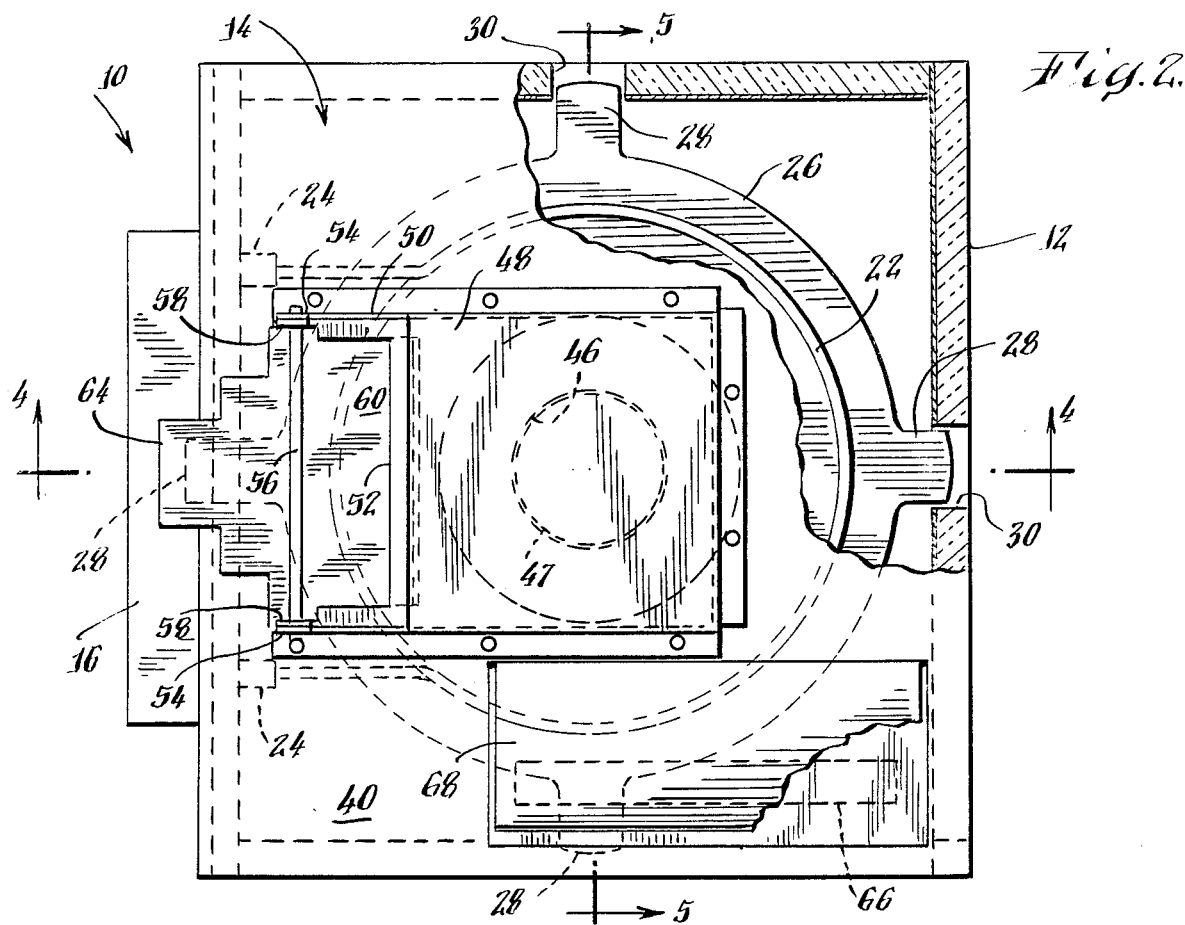
FIG. 2 is a plan view of the oven of FIG. 1, partially broken away to illustrate its internal construction.
Figure 3:
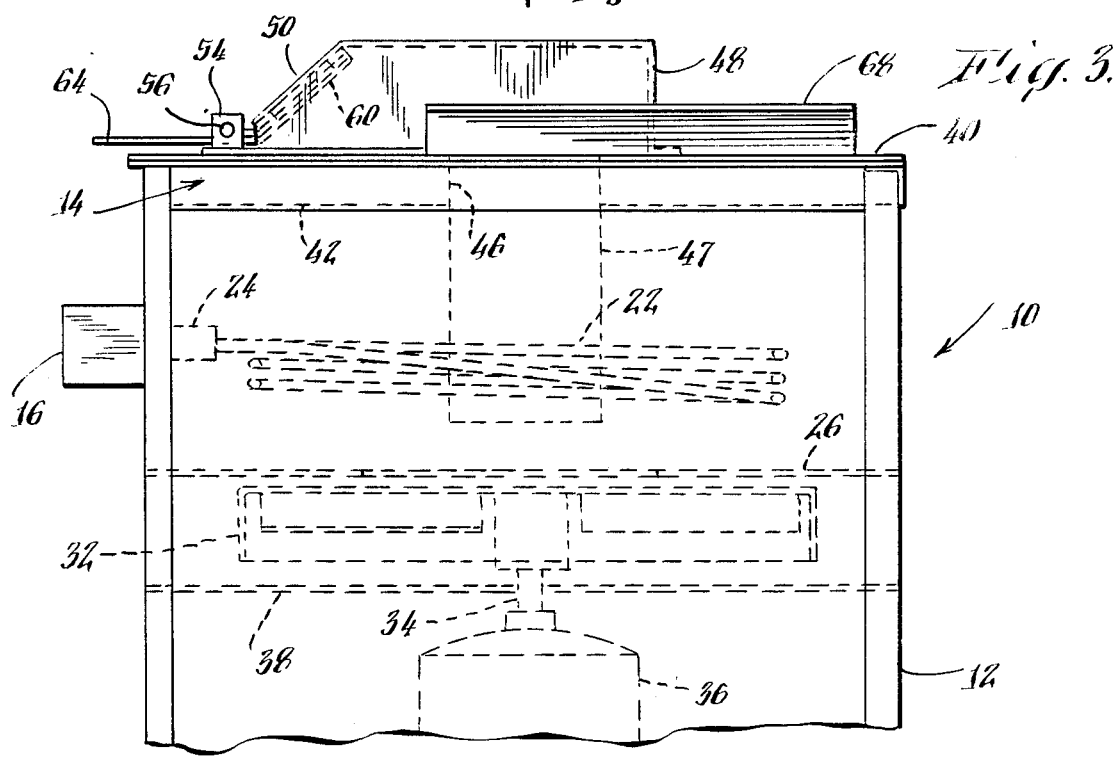
FIG. 3 is an elevational view of the oven of FIG. 2.

FIG. 6 illustrates schematically and in generalized form the control electronics for the oven of the invention. It will be understood that the heating means 19 is conventional and, accordingly, is not described in detail. Positioned within the oven 10 is a heat sensor such as a thermocouple 72. The output of thermocouple 72 is applied to one input of a differential amplifier 74. The other output to amplifier 74 is a set-point temperature input 76 which may come from a master controller. The output of the differential amplifier 74 actuates speed control circuitry 78 which, in turn, varies the speed of motor 36 as will be later described. As previously explained, this invention differs from the prior art by completely eliminating the need for relatively complex vent control mechanisms. Instead, the oven air circulating fan functions to initiate desired changes in air flow through self actuated air inlet and outlet openings.

Operation

A typical temperature program for a gas chromatograph might require, for example, that the temperature be held at 40° C. for five minutes and then climb to 250° C. at a rate of 10° C. per minute. The programmed temperature rise is achieved conventionally by control of the oven heater. During this time, the fan impeller 32 may be rotated at a relatively slow speed to circulate air within the oven and evenly distribute heat without actuating the vents.

After the maximum temperature has been reached, it is necessary to cool the oven back to the initial temperature, rapidly and precisely, to ready the instrument for another analysis. In accordance with the invention, this is achieved by increasing the speed of the motor 36. As the speed of the motor increases, the vacuum created at the center of the impeller 32 increases, as does the external pressure around the periphery of the fan, and thus the oven. This increased suction causes the air inlet door 60 to swing open, permitting an inflow of cool room air as shown by the arrows in FIG. 4. Simultaneously, the increased pressure around the periphery of the oven forces open the rubber flap 70 of air outlet opening 66. It will be noted that the air outlet opening 66 will open only enough to accommodate the excess inlet air. In other words, the air inlet and outlet openings are proportional to the volume of air flow, rather than being derived from mechanical linkages.

As the internal temperature of the oven decreases, the fan may be slowed, with corresponding decreases in the air inlet and outlet openings. Alternatively, the fan may be maintained at full speed until the desired temperature is reached. The choice depends upon the program to be followed. In any event, when the desired set-point temperature is reached, the fan may be slowed to a speed wherein the counterweight 64 closes the air inlet door 60 preventing further entrance of air and also allowing the rubber flap 70 to close over the air outlet opening 66.

It will be apparent that various adjustments may be made to this invention. For example, additional weight may be applied to the counterweight 64 or it may be held closed and then released at some particular point by a magnetic latch. Other variations and modifications will also present themselves to those skilled in the art. Accordingly, the foregoing description is to be construed as illustrative only. This invention is limited only by the scope of the following claims.

What is claimed is:

1. A gas chromatography oven apparatus comprising an oven housing forming an interior chamber,
   a chromatographic column mounted within said interior chamber,
   heater means for providing heat in said chamber and being adapted for regulation by program control for a predetermined temperature cycle to facilitate elution in said chromatographic column,
   variable-speed air circulating fan means mounted within said interior chamber for air circulation in said interior chamber,
   an air inlet in said housing for air flow from ambient atmosphere into the interior chamber,
   pressure actuated valve means for normally closing off said inlet and proportionally opening said inlet responsive to pressure imbalance between ambient atmosphere and the interior chamber produced by said fan means,
   said valve means remaining closed at a first fan speed for predetermined oven temperature distribution within said chamber and being opened at fan speeds greater than said first fan speed for drawing ambient air into said chamber,
   pressure actuated means for venting air from said interior chamber, and
   means for controlling fan speed to control air flow in said chamber and actuate said valve means in correspondence with said predetermined temperature cycle.

2. The apparatus of claim 1 wherein said fan means comprises a fan configured for inducing a relatively well defined low pressure region within said oven.

3. The apparatus of claim 2 wherein said fan means comprises a fan configured for inducing a relatively well defined high pressure region within said oven.

4. The device of claim 1 wherein said oven housing comprises a wall containing said air inlet and said pressure actuated valve means is self-contained and mounted to said wall.

5. The device of claim 4 wherein said wall is removably mounted in said oven housing.

6. The device of claim 1 wherein said means for controlling fan speed comprises means for regulating said fan means at said first fan speed for predetermined oven temperature distribution within said chamber during said temperature cycle to facilitate elution in said chromatographic column and for regulating said fan means at a second fan speed greater than said first fan speed to open said pressure actuated valve means and draw ambient air into said interior chamber to cool said interior chamber to a predetermined temperature.

7. The device of claim 6 wherein said means for regulating said fan means comprises means for progressively decreasing said fan speed from said second fan speed as said interior chamber temperature decreases with said valve means opening decreasing proportionally to fan speed.

8. The device of claim 1 wherein said venting means comprises an air outlet in said housing for air flow from said interior chamber to ambient atmosphere and a second pressure actuated valve means for closing off said outlet and proportionally opening said outlet responsive to pressure imbalance between ambient atmosphere and the interior chamber produced by said fan means.

9. The device of claim 8 wherein said first valve means comprises a hinged door having closure means tending to maintain said door in a closed position.

10. The device of claim 9 wherein said closure means is a counterweight.

11. The device of claim 10 wherein said second valve means comprises a resilient flap.

12. The device of claim 8 wherein said second valve means comprises a resilient flap.

13. The device of claim 1 wherein
    said oven housing has a square wall portion removably mounted for repositioning relative to said oven housing, said wall portion having an outer edge, said air inlet being centrally disposed in said wall portion,
    said valve means is self-contained and integrally mounted to said wall portion, and
    said venting means is disposed adjacent said outer edge integral with said wall portion,
    said wall portion, said valve means, and said venting means being removable and repositionable as a unit in said oven housing.

14. The device of claim 1 wherein
said oven housing has first and second opposing walls and third and fourth opposing walls adjacent thereto forming said interior chamber,
said air inlet comprises a conduit centrally mounted in said first wall and extending into said interior chamber toward said second wall, said conduit having an inlet end at the exterior of said oven housing and a discharge end within said interior chamber,
said fan means being positioned in spaced disposition from said first wall so as to induce a low pressure region centrally in alignment with the discharge end of said inlet conduit to draw ambient air through said conduit and so as to induce a high pressure region adjacent the third and fourth walls to drive air along said third and fourth walls toward said first wall,
said heater means being positioned adjacent said fan means such that ambient air from said inlet conduit is circulated by said heater means prior to flowing to said first wall,
said chromatography column being disposed about said inlet conduit between said first wall and said discharge end so that ambient air is circulated to said heater means prior to flowing to said chromatography column.

15. The apparatus of claim 1 wherein
operation of said fan means produces a first region of relatively high pressure within said oven housing and a second region of relatively low pressure within said housing,
said air inlet being positioned to admit ambient air into said low pressure region, and
said venting means being positioned to vent air from said high pressure region.

16. The apparatus of claim 15 wherein said fan means comprises a fan configured and positioned for inducing a relatively well defined low pressure region adjacent said air inlet and a relatively high pressure region adjacent said venting means.

17. A gas chromatography oven apparatus comprising
an oven housing forming an interior chamber and having a removably mounted oven lid,
a chromatographic column mounted within said interior chamber,
a heater means for providing heat in said chamber and configured for regulation by program control for a predetermined temperature cycle to facilitate elution in said chromatographic column,
variable-speed air circulating fan means mounted within said interior chamber for air circulation in said interior chamber,
an air inlet in said oven lid for air flow from ambient atmosphere into the interior chamber,
self-contained pressure actuated valve means for normally closing off said inlet and proportionally opening said inlet responsive to pressure imbalance between ambient atmosphere and the interior chamber produced by said fan means, said valve means being integrally mounted to said removable oven lid,
said valve means remaining closed at a first fan speed for predetermined oven temperature distribution within said chamber and being opened at fan speeds greater than said first fan speed for drawing ambient air into said chamber,
self-contained pressure actuated means for venting air from said interior chamber, said venting means being integrally mounted to said removable oven lid, and
means for controlling fan speed to control air flow in said chamber and actuate said valve means in correspondence with said predetermined temperature cycle.

18. The apparatus of claim 17 wherein
said oven lid has a circumferential portion and a central portion, said air inlet being disposed in said central portion and said venting means being disposed in said circumferential portion, and
said fan means comprises a fan configured for inducing a relatively well defined low pressure region adjacent said central portion of said oven lid and a relatively well defined high pressure region adjacent said circumferential portion such that ambient air flows through said air inlet into said low pressure region when said valve means is open and air from said chamber flows from said high pressure region out said vent means to atmosphere.

19. The apparatus of claim 18 wherein said removable oven lid has a square configuration for varied selective remounting in said housing, said air inlet and said vent means being positioned on said lid for universal alignment with said respective low and high pressure regions with said low pressure region being adjacent said air inlet and said high pressure region being adjacent said vent means so that when said valve means is open responsive to said fan means ambient air flows through said air inlet into said low pressure region and air from said chamber flows from said high pressure region out said vent means to atmosphere when said oven lid is remounted in said housing.

20. A gas chromatography oven apparatus comprising,
an oven housing forming an interior chamber,
a chromatographic column mounted within said interior chamber,
heater means for providing heat in said chamber and being adapted for regulation by program control for a predetermined temperature cycle to facilitate elution in said chromatographic column,
variable-speed air circulating fan means mounted within said interior chamber for air circulation in said interior chamber,
an air inlet in said housing for air flow from ambient atmosphere into the interior chamber,
pressure actuated valve means for normally closing off said inlet and proportionally opening said inlet responsive to pressure imbalance between ambient atmosphere and to interior chamber produced by said fan means,
said valve means remaining closed at a first fan speed for predetermined oven temperature distribution within said chamber and being opened at fan speeds greater than said first fan speed for drawing ambient air into said chamber,
pressure actuated means for venting air from said interior chamber, and
means for controlling fan speed to control air flow in said chamber and actuate said valve means in correspondence with said predetermined temperature cycle, wherein
operation of said fan means produces a first region of relatively high pressure within said oven housing and a second region of relatively low pressure within said housing, said air inlet comprises a conduit centrally mounted in said first wall and extending into said interior chamber toward said second wall, said conduit having an inlet end at the exterior of said oven housing and a discharge end within said interior chamber, said chromatography column being disposed about said inlet conduit between said first wall and said fan means, and said fan means being positioned in spaced disposition from said first wall so as to induce a low pressure region centrally to draw air centrally toward said fan means including ambient air through said conduit when said valve means is open and so as to induce a high pressure region adjacent the third and fourth walls to drive air away from said fan means toward said first wall, said means, forming a substantially nonvarying flow pattern within said interior chamber when said valve means is open and closed.

* * * * *

UNITED STATES PATENT AND TRADEMARK OFFICE
CERTIFICATE OF CORRECTION

PATENT NO. : 4,752,216
DATED : June 21, 1988
INVENTOR(S) : Ronald A. Hurrell

It is certified that error appears in the above-identified patent and that said Letters Patent is hereby corrected as shown below:

Column 6, line 54, delete "to" and replace with --the--.

Column 6, line 62, delete "and".

Column 6, line 64, delete "and actuate said valve means".

Column 6, line 66-68 through column 7, lines 1-2, delete "wherein operation of said fan means produces a first region of relatively high pressure within said housing and a second region of relatively low pressure within said housing," and replace with --said oven housing having first and second opposing walls and third and fourth opposing walls adjacent thereto forming said interior chamber,--.

Column 8, line 8, before "means", second mentioned, insert --fan--.

Signed and Sealed this

Eighteenth Day of July, 1989

Attest:

DONALD J. QUIGG

Attesting Officer

Commissioner of Patents and Trademarks